United States Patent
Otte et al.

(10) Patent No.: US 8,865,651 B2
(45) Date of Patent: Oct. 21, 2014

(54) COSMETIC ANTI-AGEING SKIN CARE COMPOSITIONS

(75) Inventors: Stephanus Cornelis Maria Otte, Heemstede (NL); Claudia Amalia Estrada Hernández, Tlalpan (MX); Annis Won, West Pennant Hills (AU)

(73) Assignee: Tupperware Products S.A., Fribourg (CH)

( * ) Notice: Subject to any disclaimer, the term of this patent is extended or adjusted under 35 U.S.C. 154(b) by 750 days.

(21) Appl. No.: 12/599,419

(22) PCT Filed: May 8, 2008

(86) PCT No.: PCT/NL2008/050278
§ 371 (c)(1),
(2), (4) Date: Feb. 9, 2010

(87) PCT Pub. No.: WO2008/136676
PCT Pub. Date: Nov. 13, 2008

(65) Prior Publication Data
US 2010/0136103 A1   Jun. 3, 2010

(30) Foreign Application Priority Data
May 8, 2007   (EP) .................................... 07107712

(51) Int. Cl.
*A61K 38/00* (2006.01)
*A61K 8/64* (2006.01)
*A61Q 19/08* (2006.01)
*A61Q 17/04* (2006.01)

(52) U.S. Cl.
CPC ............... *A61K 8/64* (2013.01); *A61K 2800/59* (2013.01); *A61K 2800/592* (2013.01); *A61Q 19/08* (2013.01); *A61Q 17/04* (2013.01)
USPC ....... 514/18.8; 514/21.7; 514/21.8; 514/21.9; 514/18.6

(58) Field of Classification Search
None
See application file for complete search history.

(56) References Cited

U.S. PATENT DOCUMENTS

| | | | |
|---|---|---|---|
| 5,718,882 A * | 2/1998 | Zamora ......................... | 424/1.69 |
| 6,969,531 B2 * | 11/2005 | Dehazya et al. ............... | 424/493 |
| 2006/0198800 A1 * | 9/2006 | Dilallo et al. .................. | 424/59 |
| 2007/0086981 A1 * | 4/2007 | Meijer et al. ................. | 424/93.2 |

FOREIGN PATENT DOCUMENTS

| | | |
|---|---|---|
| EP | 1 180 524 A1 | 2/2002 |
| EP | 1 640 041 A | 3/2006 |
| EP | 1 741 421 A | 1/2007 |
| WO | WO 2004/099237 A1 | 11/2004 |
| WO | WO 2006/053688 A | 5/2006 |

OTHER PUBLICATIONS

Cellular Skin Rx, published on the website http://www.cellularskinrx.com/ingredients.html on Aug. 19, 2006; pp. 1-6; obtained from the web Apr. 10, 2013.*
Puig A: "Synthetic Actives for Cosmetic Applications" Speciality Chemicals, vol. 22, No. 10, Nov. 2002, pp. 16-17.
Lupo Mary P: "Cosmeceutical peptides" Dermatologic Surgery, Elsevier Science, New York, NY, US, vol. 31, No. 7 Pt 2, Jul. 2005, pp. 832-836.
Garcia—Anton J.M.: "The Scientific Response to Different Types of Wrinkles" SOFW Journal, vol. 132, No. 4, 2006, pp. 8-16.
NN: "Cosmetic improvements—Peptides both natural and synthetic are finding growing applications in the cosmetics and personal care sector" Specialty Chemicals Magazine, Mar. 2006, pp. 26-29.
Karl Lintner et al: "Skin conditioning is achieved with laminin and collagen stimulation by biotinoyl tripeptide" Research Disclosure, Mason Publications, vol. 493, No. 18, May 2005.
Anonymous: "New synergistic composition for topical application against wrinkles" Research Disclosure, Mason Publications vol. 500, No. 28, Dec. 2005.
Lipotec S A: "Serilesine—An adhesion sequence from Laminin—revision 3" Internet Citation, [Online] May 2004, pp. 1-8, XP002436143 Retrieved from the Internet: URL:http://www.centerchem.com/PDFs/Seriles,_ine.pdf> [retrieved on 2007]p. 6.
International Search Report dated Apr. 2, 2009 for PCT/NL2008/050278.

* cited by examiner

*Primary Examiner* — Karlheinz R Skowronek
*Assistant Examiner* — Lianko Garyu
(74) *Attorney, Agent, or Firm* — Leydig, Voit & Mayer, Ltd.

(57) ABSTRACT

The invention is directed to an anti ageing skin care composition, more in particular a cosmetic anti aging skin care composition. The anti ageing skin care composition of the invention comprise, in a physiologically acceptable medium, (i) at least one peptide from Laminin-1 that is able to promote synthesis of Laminin-5; (ii) at least one peptide capable of at least partially inhibiting neuronal exocytosis; and (iii) at least one tripeptide producing a rapid and strong stimulation of collagen synthesis. The compositions of the present invention are effective in reducing existing wrinkles and/or preventing the formation of new wrinkles.

11 Claims, 1 Drawing Sheet

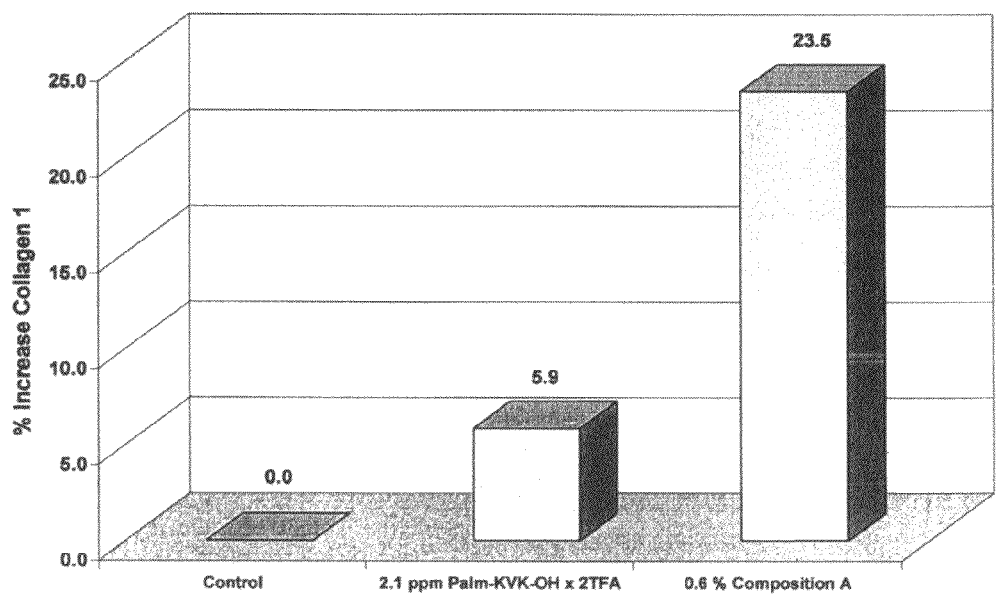

SEQUENCE LISTING

<160> NUMBER OF SEQ ID NOS: 8

<210> SEQ ID NO 1
<211> LENGTH: 82
<212> TYPE: PRT
<213> ORGANISM: Artificial Sequence
<220> FEATURE:
<223> OTHER INFORMATION: Synthetic peptide

<400> SEQUENCE: 1

```
Ala Glu Asp Ala Asp Met Arg Asn Glu Leu Glu Glu Met Gln Arg Arg
1               5                   10                  15

Ala Asp Gln Leu Ala Asp Glu Ser Leu Glu Ser Thr Arg Arg Met Leu
            20                  25                  30

Gln Leu Val Glu Glu Ser Lys Asp Ala Ile Arg Thr Leu Val Met Leu
        35                  40                  45

Asp Glu Gln Gly Glu Gln Leu Glu Arg Ile Glu Glu Gly Met Asp Gln
    50                  55                  60

Ile Asn Lys Asp Met Lys Glu Ala Glu Lys Asn Leu Thr Asp Leu Gly
65                  70                  75                  80
```

Lys Phe

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Glu Glu Met Gln Arg Arg
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic peptide

<400> SEQUENCE: 3

Glu Leu Glu Glu Met Gln Arg Arg Ala Asp Gln Leu Ala
1               5                   10

<210> SEQ ID NO 4
<211> LENGTH: 86
<212> TYPE: PRT
<213> ORGANISM: Artificial Sequence
<220> FEATURE:
<223> OTHER INFORMATION: Synthetic peptide

<400> SEQUENCE: 4

Val Asp Glu Arg Glu Gln Met Ala Ile Ser Gly Gly Phe Ile Arg Arg
1               5                   10                  15

Val Thr Asn Ala Arg Glu Asn Glu Glu Met Asp Glu Asn Leu Glu Gln
                20                  25                  30

Val Ser Gly Ile Leu Gly Asn Leu Arg His Met Ala Leu Asp Met Gly
            35                  40                  45

Asn Glu Ile Asp Thr Gln Asn Arg Gln Ile Asp Arg Ile Met Glu Lys
    50                  55                  60

Ala Asp Ser Asn Lys Thr Arg Ile Asp Glu Ala Asn Gln Arg Ala Thr
65                  70                  75                  80

Lys Met Leu Gly Ser Gly
                85

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Arg Ile Met Glu Lys Ala Asp Ser Asn Lys Thr Arg Ile Asp Glu Asp
1               5                   10                  15

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide

<400> SEQUENCE: 6

```
Ala Asp Ser Asn Lys Thr Arg Ile Asp Glu Ala Asn Gln Arg Ala Thr
1               5                   10                  15

Lys Met Leu

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino terminus of SEQ ID NO: 7 can be
      modified with an H, any amino acid, or a linear or branched acyl
      group.
<220> FEATURE:
<221> NAME/KEY: MOD_RES
<222> LOCATION: (5)..(5)
<223> OTHER INFORMATION: The carboxyl terminus of SEQ ID NO: 7 can be
      modified by the addition of amino, hydroxyl or thiol group, or
      fatty acids.

<400> SEQUENCE: 7

Ile Lys Val Ala Val
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: The amino-terminal amino acid can be
      acetylated.
<220> FEATURE:
<221> NAME/KEY: MOD_RES
<222> LOCATION: (8)..(8)
<223> OTHER INFORMATION: The carboxyl-terminal amino acid can be
      amidated.

<400> SEQUENCE: 8

Glu Glu Met Gln Arg Arg Ala Asp
1               5
```

COSMETIC ANTI-AGEING SKIN CARE COMPOSITIONS

FIELD OF THE INVENTION

The invention is directed to an anti-ageing skin care composition, more in particular a cosmetic anti-aging skin care composition.

BACKGROUND

The human skin is made up of several layers, of which accepted models usually distinguish the epidermis, the dermis, and the subcutaneous tissue. The epidermis is the outer layer of the skin and functions as a barrier to the external environment. The keratinocyte cells of the epidermis move from the bottom layer of the epidermis to the top layer building up a large amount of keratin and developing a strong protective barrier. Once these cells reach the top layer, they flake off.

The dermis is the second layer of skin, containing the structural elements of the skin, the connective tissue. There are various types of connective tissue with different functions. Elastin fibres give the skin its elasticity, and collagen gives the skin its strength.

The junction between the dermis and the epidermis is an important structure. The dermal-epidermal junction interlocks forming finger-like epidermal ridges. The cells of the epidermis receive their nutrients from the blood vessels in the dermis. The epidermal ridges increase the surface area of the epidermis that is exposed to these blood vessels and the needed nutrients.

The ageing of skin comes with significant physiological changes to the skin. The generation of new skin cells slows down, and the epidermal ridges of the dermal-epidermal junction flatten out. Whilst the number of elastin fibres increases, their structure and coherence decreases. Also the amount of collagen and the thickness of the dermis decrease with the ageing of the skin.

Collagen is a major component of the skin's extracellular matrix, providing a structural framework. During the aging process, the decrease of collagen synthesis and insolubilization of collagen fibres contribute to a thinning of the dermis and loss of the skin's biomechanical properties.

The physiological changes to the skin result in noticeable ageing symptoms often referred to as chronological-, intrinsic- and photo-ageing. The skin becomes drier, roughness and scaling increase, the appearance becomes duller, and most obviously fine lines and wrinkles appear.

The dermal-epidermal junction is a basement membrane that separates the keratinocytes in the epidermis from the extracellular matrix, which lies below in the dermis. This membrane consists of two layers: the basal lamina in contact with the keratinocytes, and the underlying reticular lamina in contact with the extracellular matrix. The basal lamina is rich in collagen type IV and laminin, molecules that play a role in providing a structural network and bioadhesive properties for cell attachment.

Laminin is a glycoprotein that only exists in basement membranes. It is composed of three polypeptide chains (alpha, beta and gamma) arranged in the shape of an asymmetric cross and held together by disulfide bonds. The three chains exist as different subtypes which result in twelve different isoforms for laminin, including Laminin-1 and Laminin-5.

The dermis is anchored to hemidesmosomes, specific junction points located on the keratinocytes, which consist of α-integrins and other proteins, at the basal membrane keratinocytes by type VII collagen fibrils. Laminins, and particularly Laminin-5, constitute the real anchor point between hemidesmosomal transmembrane proteins in basal keratinocytes and type VII collagen.

Laminin-5 synthesis and type VII collagen expression have been proven to decrease in aged skin. This causes a loss of contact between dermis and epidermis, and results in the skin losing elasticity and becoming saggy.

Recently another type of wrinkles, generally referred to as expression wrinkles, got general recognition. These wrinkles require loss of resilience, particularly in the dermis, because of which the skin is no longer able to resume its original state when facial muscles which produce facial expressions exert stress on the skin, resulting in expression wrinkles.

In the art, several attempts have been made to provide skin care compositions that reduce some of the above-mentioned skin aging symptoms.

WO-A-2005/105029 discloses synthetic hexapeptides from Laminin-1 that are said to restore the skin's normal function.

EP-A-1 180 524 discloses peptides that are useful as neuronal exocytosis inhibitor which are said to have an anti-wrinkle effect.

WO-A-2004/099237 discloses tripeptides with a skin structure improving effect.

SUMMARY OF THE INVENTION

Object of the present invention is to provide an anti-ageing skin care composition, in particular an anti-wrinkle skin care composition, that is more effective in reducing the effects of ageing on the skin than the skin care compositions of the prior art.

It was surprisingly found that this object is at least partly met by a skin care composition that addresses a combination of pivotal skin ageing expressions, and not only its underlying isolated symptoms.

Accordingly, the invention is directed to an anti-ageing skin care composition, comprising, in a physiologically acceptable medium,
(i) at least one peptide from Laminin-1 that is able to promote synthesis of Laminin-5;
(ii) at least one peptide capable of at least partially inhibiting neuronal exocytosis (e.g., SEQ ID NOS: 1-6); and
(iii) at least one tripeptide producing a rapid and strong stimulation of collagen synthesis.

The composition of the invention provides better interaction between epidermis and dermis, reduces degeneration of and replenishes collagen, and reduces the impact of underlying muscles on formation of wrinkles, thus reducing the effects of chronological ageing, photo-induced ageing, and formation of expression wrinkles.

It was surprisingly found that the combination of ingredients act together in a synergetic fashion. The at least one peptide from Laminin-1 and the at least one peptide capable of partially inhibiting neuronal exocytosis enhance the collagen synthesis, which is stimulated by the at least one tripeptide. Accordingly, the composition of the invention makes it possible to reduce, and preferably prevent, neutralise and reverse the formation of different types of wrinkles.

The invention allows the reversal of the degeneration of collagen by synergistically stimulating synthesis reactions of the skin matrix, including collagen. In addition, the composition of the invention allows preventing the degeneration of the dermal-epidermal junction, which is assumed to be involved in ageing of the skin and generation of wrinkles. Furthermore, the invention allows neutralising the effects of microtensions on the skin by relaxing the dermal contractile fibroblasts, which are assumed to be involved in the genesis of expression wrinkles.

BRIEF DESCRIPTION OF THE DRAWING

FIG. 1, shows the percent increase in collagen 1 expression in human fibroblasts treated with a negative control, Palmitoyl-KVK-OHx2TFA only or composition A.

DETAILED DESCRIPTION OF EXEMPLARY EMBODIMENTS

The peptide from Laminin-1 that is able to synthesise Laminin-5 preferably comprises a sequence from the alpha chain of laminin of the general formula (I) X-Ile-Lys-Val-Ala-Val-Y (SEQ ID NO: 7)

$$X-NH-CH(CH(CH_3)CH_2CH_3)-CO-NH-CH((CH_2)_4NH_2)-CO-NH-CH(CH(CH_3)CH_2CH_3)-CO-NH-CH(CH_3)-CO-NH-CH(CH(CH_3)CH_2CH_3)-CO-Y \quad \text{I}$$

Wherein

X represents H, an amino acid, or a linear or branched acyl group as in formula (I), and Y represents an amino-, hydroxyl or thiol group, substituted or not substituted with fatty acids.

The peptide from Laminin-1 promotes the synthesis of Laminin-5, and stimulates keratinocytes and fibroblast proliferation. This induces an improvement in skin elasticity, compactness, tonicity, and smoothness.

One particular preferred peptide is hexapeptide-10, available from the company Lipotec under the trademark Serilesine®.

The peptide capable of at least partially inhibiting neuronal exocytosis can for instance act via interference with the formation and stability of the SNARE complex, thereby reducing the release of the neuromediator acetylcholine into the synaptic spaces. An example of such a peptide is for instance a peptide comprising at least one amino acid sequence derived from the amino acid sequence of the protein SNAP 25.

As used herein, the term "sequence derived from the amino acid sequence of the protein SNAP 25" means any amino acid sequence or amino acid sequence fragment of the protein SNAP 25, defined by SEQ ID No. 1 or any amino acid sequence that differs from the sequence SEQ ID No. 1 by mutation, insertion, deletion or substitution of at least one amino acid, or by degeneracy of the genetic code, provided that it corresponds to a polypeptide having the activity of SNAP 25.

The mechanism of action of these peptides is similar to that of botulinum toxins: they affect the formation and/or stability of the fusion protein complex (SNARE), the role of which it is to mediate neuronal exocytosis. The SNARE complex is a core of membrane proteins consisting of Synaptosomal associated protein (25 kDa, SNAP 25), synaptobrevin and syntaxin.

The at least one peptide capable of at least partially inhibiting neuronal exocytosis may have an amino acid sequence comprising from 3 to 30 amino acids such as from 6 to 19 amino acids, in which the N-terminal amino acids may be acetylated and/or the C-terminal amino acid may be amidated.

In one embodiment, a peptide capable of at least partially inhibiting neuronal exocytosis that may be used is the hexapeptide defined by SEQ ID No. 2 (acetyl hexapeptide-8).

In another embodiment, a peptide capable of at least partially inhibiting neuronal exocytosis that may be used is an octapeptide chosen from the sequence defined by SEQ ID No. 3.

It is also possible to use a peptide capable of at least partially inhibiting neuronal exocytosis chosen from:

(i) a peptide that is substantially homologous with the peptides defined by SEQ ID No. 2 and SEQ ID No. 3;

(ii) a peptide that is functionally equivalent to the peptides defined by SEQ ID No. 2 and SEQ ID No. 3;

(iii) a cosmetically acceptable salt of the peptides defined by SEQ ID No. 2 and SEQ ID No. 3; and (iv) a peptide defined by SEQ ID No. 2 or SEQ ID No. 3 that has undergone reversible chemical changes.

The hexapeptide mentioned above is available from the company Lipotec under the trademark Argireline® it comprises a sequence of 6 amino acids: glutamyl-glutamyl-methionyl-glutaminyl-arginyl-arginyl (SEQ ID NO: 2), wherein the first (N-terminal) is acetylated, and the last (C-terminal) is amidated.

In a preferred embodiment the octapeptide mentioned above is acetyl glutamyl heptapeptide-3, available from the company Lipotec under the name SNAP-8 (SEQ ID NO: 8).

As used herein, the term "substantially homologous" peptide or amino acid sequence means an amino acid sequence that is at least 60%, such as 80%, and further, such as at least 95% identical to the sequence SEQ ID No. 2.

The term "cosmetically acceptable salt of such peptide" means metal salts or salts formed by addition of suitable acids or bases, which may be obtained from a reaction with the peptides disclosed herein, according to the methods known to those skilled in the art.

Organic salts of peptides that may be mentioned include, for example, peptide gluconate, peptide acetate, peptide citrate, peptide oleate and peptide oxalate.

Mineral salts of peptides that may be mentioned include, for example, peptide chloride, peptide borate, peptide sulphate and peptide carbonate.

As "reversible chemical modifications" of the peptide so as to increase its bioavailability and its ease of passing through epithelial tissue without affecting its capacity to inhibit the type-L calcium channels, examples that may be mentioned include the esterification reaction of the carboxylate groups of the amino acids glutamic acid and aspartic acid with an acetylmethyl group, thus removing the negative charge from the amino acid and increasing its hydrophobicity.

It is also possible to use, in the context of the invention, at least one peptide capable of at least partially inhibiting neuronal exocytosis chosen from:

a) a peptide comprising a sequence ranging from 3 to 30 amino acids contained in SEQ ID No. 1 (protein SNAP 25);

b) a peptide comprising a sequence ranging from 6 to 19 amino acids derived from the N-terminus of the protein SNAP 25, chosen from the peptides defined by SEQ ID No. 2 and SEQ ID No. 3;

c) a peptide comprising a sequence ranging from 6 to 19 amino acids derived from the C-terminus of the protein SNAP 25, chosen from the peptides defined by SEQ ID No. 5 and SEQ ID No. 6;

d) a peptide mixture comprising at least one peptide ranging from 3 to 30 amino acids chosen from those described in a), b) and c) and at least one peptide ranging from 3 to 30 amino acids contained in SEQ ID No. 4 ((COOH) peptide sequence); and e) a peptide mixture comprising at least one peptide chosen from those formed by the peptides defined by SEQ ID No. 2 and SEQ ID No. 3 (N-terminus) and at least one peptide chosen from the peptides defined by SEQ ID No. 5 and SEQ ID No. 6 (C-terminus).

The term "tripeptide producing a rapid and strong stimulation of collagen synthesis" means any tripeptide and tripeptide derivative of general formula (II)

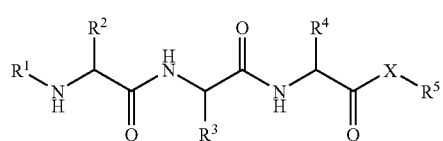

wherein $R^1$ represents H, —C(O)—$R^6$, $SO_2$—$R^6$ or —C(O)—$XR^6$ $R^2$ and $R^4$, independent of one another, represent $(CH_2)_n$—$NH_2$ or $(CH_2)_3$—$NHC(NH)NH_2$, n equals 1-4, $R^3$ represents linear or branched $C_1$-$C_4$-alkyl that is optionally substituted by hydroxyl, $R^5$ and $R^6$, independent of one another, represent hydrogen, optionally substituted $(C_1$-$C_{24})$-alkyl, optionally substituted $(C_2$-$C_{24})$-alkenyl, optionally substituted phenyl, optionally substituted phenyl-$C_1$-$C_4$-alkyl or 9-fluorenylmethyl, X represents oxygen (—O—) or —NH—; or $XR^5$ with X=O also represents α-tocopheryl esters, tocotrienyl esters or retinyl esters, as racemates or as pure enantiomers, as well as the salts thereof for application as cosmetic actives.

These tripeptides act advantageously on the skin structure by specifically stimulating the growth factor TGFβ1, which is responsible for the anabolism of macromolecules in the skin matrix. This activates the synthesis reactions in the skin matrix.

The mechanism of action of these peptides is similar to thrombospondin-1 (TSP-1), a protein secreted by skin cells: they activate latent TGFβ1, the role of which is to stimulate synthesis reactions of the skin matrix, including collagen and elastin.

The above used, general terms are defined as follows: alkyl comprises linear as well as branched alkyl groups. Examples thereof are methyl, ethyl, propyl, n-butyl, n-pentyl, n-hexyl, n-heptyl, n-octyl, n-nonyl, n-undecanyl, n-dodecanyl, n-tridecanyl, n-hexadecanyl, n-heptadecanyl, n-octadecanyl or n-nonadecanyl as unbranched residues, and isopropyl, tert-butyl, isobutyl, sec-butyl, isomayl as branched residues. $R^5$ and $R^6$, as optionally substituted alkyl and independent of one another, preferably represent $(C_2$-$C_{24})$-alkyl, preferably $(C_3$-$C_8)$-alkyl.

As used herein, "alkenyl" has the denotation of a mono- or poly-unsaturated, optionally substituted alkyl group, such as e.g. 8(Z)-heptadecenyl, 8(Z), 11(Z)-heptadecadienyl, 4(Z), 7(Z), 10(Z), 13(Z)-nonadecatetraenyl, 8(Z)-11-hydroxyoctadecenyl.

As used herein, "α-tocopheryl" means (D)-, (L)- or (DL)-2,5,7,8-tetramethyl-2-(4',8',12'-trimethyltridecyl)-6-chromanyl, tocotrienyl means any isomer of 2,5,7,8-tetramethyl-2-(4',8',12'-trimethyl-3',7',11'-tridecatrienyl)-6-chromanyl and retinyl means 3,7-dimethyl-9-(2,6,6-trimethyl-1-cyclohexenyl)-2,4,6,8-nonatetraen-1-yl.

The compounds of formula (II) together with acids can form mono- or polyvalent, homogeneous or mixed salts, e.g. with inorganic acids, such as hydrochloric acid, hydrobromic acid, sulphuric acid or phosphoric acid; or with appropriate carboxylic acids, e.g. aliphatic mono- or dicarboxylic acids, such as formic acid, acetic acid, trifluoracetic acid, trichloroacetic acid, propionic acid, glycolic acid, succinic acid, fumaric acid, malonic acid, maleic acid, oxalic acid, phthalic acid, citric acid, lactic acid or tartaric acid; or with aromatic carboxylic acids, such as benzoic acid or salicylic acid; or with aromatic-aliphatic carboxylic acids, such as mandelic acid or cinnamic acid; or with heteroaromatic carboxylic acids, such as nicotinic acid; or with aliphatic or aromatic sulphonic acids, such as methanesulphonic acid or toluenesulphonic acid. Dermatologically tolerated salts are preferred.

The general formula (II) includes all the possible isomeric forms as well as mixtures thereof, e.g. racemic mixtures and mixtures of rotamers.

One particular tripeptide mentioned above is palmitoyl-lysyl-valyl-lysine bistrifluoracetate salt, available from the company Pentapharm under the trademark Syn®-Coll.

The compounds of formula (II) can be used in concentrations ranging between 0.5 and 5000 ppm (w/w), preferably between 1 and 1000 ppm (w/w), in the cosmetic end product. The compounds of formula (II) can be used as a solution, a dispersion, an emulsion or encapsulated in carriers such as macro-, micro- or nanoparticles or in microsponges or absorbed on powdered organic polymers, talc, bentonite and further inorganic carriers.

It is preferred that the composition of the invention also comprises hyaluronic filling spheres, for instance those available from former Engelhard, which is now owned by BASF. Such filling spheres can be used to fill up existing wrinkles.

The composition of the invention can be applied in any kind of vehicle. The composition can for instance be applied in the form of an oil in water emulsion, a water in oil emulsion, an aqueous solution, a gel, a powder or a compact powder. In a preferred embodiment, the composition of the invention is a water based cream, which may be topically applied to the skin.

The composition of the invention can comprise different kinds of oils or waxes that are used to give the final product a desired consistence and provide the final product with a pleasing touch. As oils or waxes which may be used in the invention, mention may be made, for example, of mineral oils (such as petrolatum liquidum or hydrogenated polyisobutene), oils or waxes of plant origin (such as apricot kernel oil), oils or waxes of animal origin (such as lanolin), silicone oils (such as dimethicone or cyclomethicone), fluoro oils (such as perfluoropolyethers), fatty alcohols (such as cetearyl alcohol) and fatty acids. Specific examples of oils and waxes that can be used in accordance with the invention are cetyl ester, Polysorbate 60, dicaprylyl ether, PPG-3 benzyl ether myristate, caprylic acid triglycerides and tridecyl neopentanoate.

Also emulsifiers may be comprised in the composition of the invention. Emulsifiers can assist in mixing the lipids with the water. Such mixing can be performed under intense stirring and the application of heat. Suitable emulsifiers include sorbitan monooleate and Polysorbate 80. The composition of the invention can further comprise a fragrance substance for giving the final product a pleasing aroma.

Also thickeners can be included in the composition of the invention. Typical thickeners are carbomers. But also any suitable alternative may be used.

The composition of the invention can further comprise preservative compounds, which can be selected from a wide range of molecules, including parabens (e.g. methylparaben, ethylparaben, propylparaben and iso-butylparaben), formaldehyde releasers (e.g. imidazolidinyl urea and diazolidinyl urea), and butylated hydroxyl toluene (BHT).

In addition, the composition of the invention can comprise chelating agents which are able to neutralise small amounts of metals that may be present in the product, for instance originating from the containers in which the product is mixed.

The compositions of the invention can be used in a method of cosmetic treatment of the skin, in particular human skin, which method comprises applying a composition according to any of the previous claims to at least a part of the outer surface of said skin.

The present invention is also directed to the use of a composition as described herein in the preparation of an anti-ageing skin care composition.

The invention is illustrated in more detail by the following non-limiting example.

EXAMPLE

Demonstration of a Synergistic Effect of the Combination of Syn®Coll with SNAP 0.8 and Serilesine® on Synthesis of Collagen 1

A composition was prepared in the laboratory by an experienced lab technician of a development laboratory using laboratory equipment (including stirrers, homogenizer, incubators and refrigerator).

A batch of 100 g of composition A (see Table 1) was prepared at ambient temperature, by dissolving the active ingredients in water. Where necessary, suitable co-solvents were used as instructed by the suppliers. Next, preservative (0.6% Germaben II) was dissolved into the solution.

TABLE 1

| Composition A ingredients (%) | |
|---|---|
| Demineralised water | q.s |
| Palmitoyl KVK-OH × 2TFA (10 mM) | 4.00 |
| SNAP 8 | 12.00 |
| Serilesine ® | 12.00 |
| Germaben II | 0.60 |
| Total | 100.00 |

The collagen 1 synthesis capability of a 0.6% solution of composition A was studied against 2.5 µM Palmitoyl KVK-OH×2TFA and a control without actives, according to the method described by Imfeld et al. (2006), *Proceedings of the 24th IFSCC Congres,* Osaka, Japan.

Surprisingly, it was noted that the components of composition A act synergistically on the increase of collagen 1 expression in human fibroblasts. This is illustrated by FIG. 1. The synergistic effect represents a mean increase of collagen 1 level improvement of 17.6 pp, compared to the sample containing similar levels of Palmitoyl-KVK-OH×2TFA only.

The invention claimed is:

1. Anti-ageing skin care composition, comprising, in a physiologically acceptable medium,
   (i) a modified pentapeptide or hexapeptide of the amino acid sequence Ile-Lys-Val-Ala-Val (SEQ ID NO: 7) wherein the SEQ ID NO: 7 amino terminus can be modified by the addition of a H, any amino acid, or a linear or branched acyl group, and the carboxyl terminus of SEQ ID NO: 7 may be modified by the addition of an amino, hydroxyl, or thiol group, substituted or not substituted with fatty acids;
   (ii) an octapeptide with the amino acid sequence of Glu-Glu-Met-Gln-Arg-Arg-Ala-Asp (SEQ ID NO: 8), wherein the N-terminal is acetylated and the C-terminal is amidated; and
   (iii) a palmitoyl-lysyl-valyl-lysyl bistrifluoracetate salt, wherein said composition increases collagen I expression in human fibroblast.

2. The composition according to claim 1, further comprising at least one active agent chosen from the group consisting of a desquamating agent; a moisturizer; a depigmenting agent; a propigmenting agent; an anti-glycation agent; an agent for stimulating the synthesis of dennal or epidermal macromolecules; an agent for preventing the degeneration of dennal or epidermal macromolecules; an agent for stimulating the synthesis of dennal or epidermal macromolecules and for preventing their degeneration; an agent for stimulating fibroblasts proliferation; an agent for stimulating keratinocytes proliferation; an agent for stimulating fibroblasts and keratinocytes proliferation; an agent for stimulating keratinocytes differentiation; a derma-relaxant; a filling and swelling agent; a tightening agent; an antipollution agent; a free-radical scavenger; an agent that acts on capillary circulation; and an agent that acts on the energy metabolism of cells.

3. The composition according to claim 2, wherein the filling and swelling agent is encapsulated in carriers chosen from the group consisting of macroparticles, microparticles, nanoparticles, microsponges, and nanospheres or the filling and swelling agent is absorbed on powdered organic polymers, talc, bentonite, and inorganic carriers.

4. The composition according to claim 2, wherein the swelling agent is a nanosphere filled with hyaluronic acid or a derivative thereof.

5. The composition according to claim 1, further comprising at least one adjuvant chosen from the group consisting of a hydrophilic gelling agent, a lipophilic gelling agent, a hydrophilic active agent, a lipophilic active agent, a solvent, a preserving agent, a filler, a fragrance, a screening agent, an odour absorber, a pigment, and a colouring agent.

6. The composition according to claim 5, wherein the at least one adjuvant is present in an amount ranging from 0.01% to 20% by weight, based on the total weight of the composition.

7. The composition according to claim 1, wherein the composition is in a form chosen from the group consisting of a gelled aqueous solution, a lotion dispersion, a two-phase lotion, an O/W emulsion, an W/O emulsion, a W/O/W emulsion, an O/W/O emulsion, an ionic vesicular dispersion, and a non-ionic vesicular dispersion.

8. The composition according to claim 7, wherein the composition is in the form of an O/W emulsion.

9. The composition according to claim 1, further comprising at least one photoprotective agent chosen from the group consisting of UVA-active organic photoprotective agents UVA-active mineral photoprotective agents, UVB-active organic photoprotective agents, and UVB-active mineral photoprotective agents.

10. The composition according to claim 9, wherein the at least one photoprotective agent is present in an amount ranging from 0.1% to 20% by weight, based on the total weight of the composition.

11. Method of cosmetic treatment of the skin, in particular human skin, comprising applying a composition according to claim 1 to at least a part of the outer surface of said skin.

* * * * *